United States Patent [19]

Kim

[11] Patent Number: 5,244,790
[45] Date of Patent: Sep. 14, 1993

[54] MICROORGANISMS FOR PREPARING TRADITIONAL KOREAN SOYBEAN PASTE AND THE METHOD FOR THE PRODUCTION OF SOYBEAN PASTE BY USING THE SAME

[76] Inventor: Jong K. Kim, 201-502, Garden Heitz, Whanggum-Dong 100, Soosung-Ku, Taeku-Shi, Rep. of Korea

[21] Appl. No.: 808,504

[22] Filed: Dec. 17, 1991

[51] Int. Cl.$^5$ .......................... C12P 39/00; C12P 1/06; C12P 1/04; A23G 1/02
[52] U.S. Cl. ..................................... 435/42; 435/169; 435/170; 435/822; 435/836; 435/839; 426/44; 426/52; 426/629
[58] Field of Search ................. 435/42, 170, 169, 836, 435/839, 822; 426/629, 44, 52

[56] References Cited

PUBLICATIONS

Kiuchi et al., "Isolation of Microorganisms from Specially Prepared Miso" Rept. Natl. Food Res. Inst., No. 45, 14-18 (1984).

Shinohara, "Thermal Processing of Canned Miso Soup", p. 523, lines 5-8, 1985.

Kwon et al., "The Characteristics of Bacteria Isolated from Ordinary Korean Soy Sauce and Soybean Paste," Journal of the Korean Agricultural Chemical Society, vol. 29, No. 4, Dec. 1986.

T. Yokotsuka, "Fermented Protein Foods in the Orient, with Emphasis on Shoyu and Miso in Japan," Chapter 5 in Wood, ed., Microbiology of Fermented Foods, vol. 1, Elsevier Applied Science Publishers, New York.

Chang et al., "Statistical Analysis for the Relationship Between Gas Chromatography Profiles of Korean Ordinary Soybean Paste Flavor and Sensory Evaluation," Kor. J. Appl. Microbiol. Bioeng., V. 12, No. 2, 147-52, 1984.

Kyung et al., "Development of Excellent Mutants for the Manufacture of Ordinary Korean Soy Sauce and Soybean Paste," Kor. J. Appl. Microbiol. Eng., vol. 15, No. 1, pp. 21 28, 1987.

Kim et al., "Genetic Breeding of Korean Soybean Paste-Fermenting Bacillus sp. by UV Mutation," Journal of the Korean Agricultural Chemical Society, vol. 32, No. 2, pp. 148'153, Jun. 1989.

Kim et al., "Indole Content and Microorganisms Producing Indole of Traditional Korean Soybean Paste," Environmental Research, vol. 11, No. 1, pp. 31-36.

Kim et al., "Genetic Breeding of Korean Soy Sauce-Fermenting Bacillus by UV Mutation," Journal of the Korean Agricultural Chemical Society, vol. 31, No. 4, Dec. 1988, pp. 346-350.

Song et al., "Flavor Components Produced by Microorganism During Fermentation of Korean Ordinary Soybean Paste," Kor. J. Appl. Microbiol. Bioeng., vol. 12, No. 2, pp. 147-152, 1984.

Kim et al., "Characteristics of Aroma Produced by Microorganisms During Fermentation of Ordinary Korean Soy Sauce," vol. 5, 1986.

Kim et al., "Distribution of Volatile Organic Acids in Traditional Korean Soy Sauce and Microorganisms Producing the Organic Acids," vol. 9, 1990.

Kim et al., "Pyrazines in Traditional Korean Soybean Paste and Soybean Paste Produced by Bacillus sp. SPB1," Environmental Research, vol. 11, No. 1, 1991, pp. 37-45.

*Primary Examiner*—David M. Naff
*Assistant Examiner*—L. Blaine Lankford
*Attorney, Agent, or Firm*—Millen, White, Zelano, & Branigan

[57] ABSTRACT

The present invention relates to microorgaisms which produce the aroma and flavor of traditional Korean soybean paste. The present invention also relates to a method for producing the soybean paste which comprises inoculating a pure boiled soybean medium with *Bacillus subtilis* PM3 or *Bacillus subtilis* SS9 and culturing it at 25°-35° C. for 40-60 days to produce the soybean paste. The present invention further relates to a method for producing the soybean paste, which comprises inoculating a pure boiled soybean medium with *Bacillus subtilis* PM3 or *Bacillus subtilis* SS9 together with a fusant yeast ST723-F31 or *Bacillus licheniformis* SSA3-2M1 and culturing them at 25°-35° C. for 40-60 days to produce the soybean paste.

7 Claims, 4 Drawing Sheets

MICROORGANISMS FOR PREPARING TRADITIONAL KOREAN SOYBEAN PASTE AND THE METHOD FOR THE PRODUCTION OF SOYBEAN PASTE BY USING THE SAME

FIELD OF THE INVENTION

The present invention relates to microorganisms for preparing traditional Korean soybean paste and the method for the production of soybean paste by using the same.

DESCRIPTION OF THE PRIOR ART

Conventionally soybean paste had been made by preparing a Meju(a Korean fermented soybean) from boiled soybeans, immersing the meju in the brine at room temperature for 2 to 3 months to carry out the first fermentation and then subjecting the preliminarily fermented meju, after separating from the brine, to a secondary fermentation at room temperature for more than 4 months.

In the conventional method, the meju is prepared by fermenting boiled soybeans at room temperature for 2 to 3 months and many bacteria or fungi, which are present in the air, are involved in the fermention.

Therefore, the quality of the produced Meju for example, flavor, aroma or color varies depending on the kind of bacteria or fungi involved in the fermention.

In order to avoid the above drawback, an attempt was made to prepare the Meju by using *Aspergillus oryzae*. The method has advantages in that the produced Meju has a homogeneous quality and that the production period is shortened. When using the strains of *Aspergillus oryzae*, the Meju can be prepared within 4 or 5 weeks. Industrial production of soybean paste employs *Aspergillus oryzae* to prepare the Meju.

However, the latter method also has disadvantage that an introduction of fungi or bacteria in the air into the fermentation jar is required for the production of the soybean paste. The air born bacteria is necessary because the Meju prepared by using *Aspergillus oryzae* cannot give the characteristic aroma of the soybean paste. Therefore, the quality of the soybean paste varies depending on the kind of the bacteria or fungi introduced during the fermentation.

Thus, the conventional processes have the following disadvantages:

first, it takes a long time to prepare the soybean paste, thus, at least 6 to 7 months are required to prepare the soybean paste;

second, it is difficult to standardize the quality of the soybean paste. Qualities such as flavor, aroma or color of the product vary because numerous microorganisms, which are originally present in the Meju or introduced from the air during the fermentation, are involved in the preparation of the soybean paste;

third, the quality of the soybean paste frequently deteriorates, for example, the color of the surface of the soybean paste is changed from yellow oak to black with the lapse of time; and fourth, it is difficult to prepare a standardized product on an industrial scale.

Therefore, there still remains a need for providing a microorganism which is capable of producing the flavor and aroma of traditional Korean soybean paste and does not produce a black pigment. There also remains a need for providing a process for preparing the soybean paste which makes it possible to produce a standardized product in a short period of time.

Under these circumstances, the present inventor has made an extensive study to isolate microorganisms which are capable of producing the flavor and aroma of traditional Korean soybean paste. And as a result thereof, I found that strains of *Bacillus subtilis* are capable of producing the flavor and aroma of the soybean paste and accomplished the present invention.

SUMMARY OF THE INVENTION

Thus, an object of the invention is to provide strains of *Bacillus subtilis* which are capable of producing the flavor and aroma of traditional Korean soybean paste and does not produce a black pigment.

Another object of the invention is to provide a process for the production of the soybean paste which comprises inoculating with the strains of *Bacillus subtilis* the smashed boiled soybean medium and culturing them at 25° to 35° C. for 40 to 60 days.

Another object of the invention is to provide a process for the preparation of the soybean paste which comprises inoculating the smashed boiled soybean medium with the strains of *Bacillus subtilis* together with the fusant yeast ST723-F31 or *Bacillus licheniformis* SSA3-2M1 and culturing them at 25° to 35° C. for 40 to 60 days.

A more complete appreciation of the invention, and many of the attendant advantages thereof, will be readily perceived as the said invention becomes better understood by reference to the annexed drawings and the detailed description of the invention. Other objects, advantages and features of the present invention will also become apparent to those skilled in the art from the following description.

DETAILED DESCRIPTION OF THE INVENTION

According to the invention, there are provided novel microorganisms which are capable of producing the flavor and aroma of traditional Korean soybean paste. These strains are obtained by isolating the microorganisms from home made soy sauce and soybean paste, which are aged for more than one year, by known methods, for example the method described by C. H. Collins and L. Lyne, Microbial methods 4th. Ed.(1976) or W. F. Harrigan and E. Micane, Laboratory methods in food and dairy microbiology (1976), culturing the microorganisms in the boiled soybean medium and selecting two strains producing the flavor and aroma of the Korean traditional soybean paste according to the Korean Industrial Standards(KIS): Organoleptic test of flavor, Industrial Advancement Administration, KSA-7002(1977) or KIS: General organoleptic test, Industrial Advancement Administration, KSA-7001(1976). The seed and culture media containing the boiled soybeans, which are employed in the present invention, are provided for the first time by the present inventor. These boiled soybean-containing media make it possible to cultivate and screen the strains of Bacillus subtilis according to the present invention.

The pure boiled soybean medium may be prepared as follows: Soybeans(Glyone max. L) are immersed in water for 14 to 17 hours, boiled at 100° to 110° C. for 2 to 4 hours and smashed. The ratio of water to the smashed soybeans is about 2.3–2.7:1. Salt is added to the concentration of 10% of water content. 300 g of the smashed boiled soybeans are placed in 500 ml flask and sterilized with the steam under the pressure of 14–16 atm. at 115°–125° C. for 35–45 min.

Two strains producing the flavor and aroma of the Korean traditional soybean paste, which isolated and selected according to the above-mentioned method, are designated as PM3 an SS9, respectively.

To identify the strains PM3 and SS9 according to the invention, the cultural, morphological and physiological characteristics were examined and the results were shown in Table 1.

TABLE 1

Microbiological Characteristics

| Characteristics | Strains SS9 | PM3 |
|---|---|---|
| Gram stain | + | + |
| Stain of the spore | + | + |
| Size of the cell (diameter 1.0 μm) | − | − |
| Roundness of the spore | − | − |
| Swollen of the sporangium | − | − |
| Lysis by catalase | + | + |
| Anaerobic growth | + | − |
| Voges-Proskauer test | + | + |
| Voges-Proskauer test at pH 6 | + | + |
| Voges-Proskauer test at pH 7 | + | + |
| Formation of acid from D-glucose | + | + |
| Formation of acid from L-arabinose | + | + |
| Formation of acid from D-xylose | + | + |
| Formation of acid from D-mannitol | + | + |
| Formation of gas from gluose | − | − |
| Hydrolysis of casein | + | + |
| Hydrolysis of gelatin | + | + |
| Hydrolysis of starch | + | + |
| Hydrolysis of tyrosine | − | − |
| Use of citrate | − | − |
| Use of propionate | − | − |
| Deamination of phenylalanin | − | − |
| Egg-yolk lecithinase | + | − |
| Reduction of nitrate to nitrite | + | + |
| Formation of indole | + | + |
| Formation of dihydroxyacetone | + | + |
| Requirement for NaCl and KCl | − | − |
| Requirement for alantoin and urate | − | − |
| Growth at pH 6.8 | + | + |
| Growth at pH 5.7 | + | + |

TABLE 1-continued

Microbiological Characteristics

| Characteristics | Strains SS9 | PM3 |
|---|---|---|
| Growth in 2% NaCl | + | + |
| Growth in 5% NaCl | + | +. |
| Growth in 7% NaCl | + | + |
| Growth in 10% NaCl | + | + |
| Growth at 5° C. | − | − |
| Growth at 10° C. | + | + |
| Growth at 30° C. | + | + |
| Growth at 40° C. | + | + |
| Growth at 50° C. | + | + |
| Growth at 55° C. | − | + |
| Growth at 65° C. | − | + |
| Growth in the presence of lysozyme | − | − |

*Note
+: positive
−: negative

Based on the results shown in Table 1, the strains PM3 and SS9 were identified by reference to N. S. Mair et al., Bergey's manual of systematic Bacteriology Volume 2(1986) and R. E. Gord et al., The Genue Bacillus, Agricultural Handbook No. 427(1973).

The strains SS9 and PM3 were identified as Bacillus subtilis by the following facts: the microbiological characteristics of the strain SS9 are similar to those of Bacillus subtilis in Bergey's manual except that anaerobic growth, Voges-Proskauer test at pH>7, availability for citrate, egg-yolk lecithinase and formation of indole, and are similar to those of Bacillus subtilis in the Genus Bacillus except that growth at 5° C. and 55° C., and egg yolk licithinase; and the microbial characteristics of the strain PM3 are similar to those of Bacillus subtilis in Bergey's manual except that Voges-Proskauer test at pH>7, availability for citrate, formation of indole, growth at 55° to 65° C. and growth in the presence of lysozyme, and are similar to those of Bacillus subtilis in the Genus Bacillus except that growth at 5° C. and 65° C. and growth in the presence of lysozyme.

The Bacillus subtilis PM3 and Bacillus subtilis SS9 have been deposited at Korean Collection for Type Culture in Daejon, Korea on Nov. 21, 1991 under the Budapest Treaty and received an Accession numbers of KCTC 0025BP and KCTC 0026BP, respectively.

Resistance Against Salt

Bacillus subtilis SS9 and Bacillus subtilis PM3 were examined for their resistance against salt. Thus, Bacillus subtilis SS9 and Bacillus subtilis PM3 were cultured in the solid or liquid propagation medium composed of glucose 2.0%, polypeptone 0.5%, yeast extract 0.5%, $KH_2PO_4$ 0.1% and $MgSO_4$ 2.0% (pH 7.0), to which salt of various concentrations shown in Table 2 was added, at 37° C. for 7 days. After the cultivation, the growth of the strains was determined with the naked eye and the results were shown in Table 2.

TABLE 2

Growth rate depending on the salt concentrations

| Medium Strain | Conc. of salt (%) | | | | | | | | | | | |
|---|---|---|---|---|---|---|---|---|---|---|---|---|
| | 5 | | 7 | | 10 | | 12 | | 15 | | 18 | |
| | S* | L** | S | L | S | L | S | L | S | L | S | L |
| SS9 | ++ | + | +++ | + | +++ | + | ++ | + | + | + | − | − |

TABLE 2-continued

| | | Growth rate depending on the salt concentrations | | | | | | | | | | |
|---|---|---|---|---|---|---|---|---|---|---|---|---|
| | | Conc. of salt (%) | | | | | | | | | | |
| | | 5 | | 7 | | 10 | | 12 | | 15 | | 18 |
| Medium Strain | S* | L** | S | L | S | L | S | L | S | L | S | L |
| PM3 | +++ | + | +++ | + | +++ | + | ++ | + | ++ | + | − | − |

Note
*S (Solid medium): +++ = colony diameter is more than 5 mm, ++ = colony diameter is 3 to 5 mm, + = colony diameter is 0 to 3 mm, − = no growth
**L (Liquid medium): + = growth, − = no growth As shown in Table 2, *Bacillus subtilis* SS9 and *Bacillus subtilis* PM3 shows considerably strong resistance against salt because both can grow in a 15% salt concentration.

Resistance Against Sugar

In order to examine the resistance against sugar, *Bacillus subtilis* SS9 and PM3 were cultured in the same medium as described for Resistance against salt to which sugar of various concentrations shown in Table 3 was added in place of salt at 37° C. for 7 days. After the cultivation, the growth of the strains was determined with the naked eye and the results were shown in Table 3.

TABLE 3

| | | Growth rate depending on the sugar concentrations | | | | | | | | |
|---|---|---|---|---|---|---|---|---|---|---|
| | | Conc. of sugar (%) | | | | | | | | |
| | | 30 | | 35 | | 40 | | 45 | | 50 |
| Medium Strain | S* | L** | S | L | S | L | S | L | S | L |
| SS9 | ++++ | + | ++++ | + | +++ | + | ++ | + | + | + |
| PM3 | +++ | + | +++ | + | +++ | + | ++ | + | + | + |

Note
*S (Solid medium): ++++ = colony diameter is more than 8 mm, +++ = colony diameter is 5 to 8 mm, ++ = colony diameter is 3 to 5 mm, + = colony diameter is 0 to 3 mm.
**L (Liquid medium): + = growth.

As shown in Table 2, *Bacillus subitilis* SS9 and PM3 showed such a high resistance against sugar that they grew in a 50% sugar concentration.

Identification and Characterization of the Aroma Components Produced by *Bacillus subtilis* SS9 and PM3

In order to identify and characterize the aroma components produced by *Bacillus subtilis* SS9 and PM9 cultured in the pure soybean medium, the whole volatile components produced by the strains were extracted and the neutral fractions which produce the characteristic aromas of traditional Korean soybean paste were isolated. The neutral fractions were concentrated and subjected to gas chromatography. Each peaks was identified and examined for its aroma characteristics.

(1) Extraction of Volatile Components

Apparatus for simultaneous steam distillation-extraction of T. H. Schults et al., J. Agric. Food Chem., 25(3), 446-449(1977), which is a modification of the method used by G. B. Nickerson, S. T. Linkens, Proc. Am. Soc. Brew. Chem., 5(1964) was employed for extracting the volatile components produced by *Bacillus subtilis* SS9 and PM3 cultured in the pure soybean medium.

*Bacillus subtilis* SS9 or PM3 was cultured in the medium containing pure boiled soybeans at 30° C. for 40 days. The culture(300 g), to which 300 g of water was added, was placed in the sample vessel and diethyl ether (100 ml) was placed in the solvent vessel. The solvent was circulated while maintaining the temperature at 40° C. and then the temperature was raised until the sample boiled. The extraction was carried out for 2 hours.

(2) Fractionation of the Volatile Components

The volatile components were fractionated in accordance with M. Fujimaki, T. Tsugita and T. Kuratai, Agric. Biol. Chem., 41(9), 1721-1725(1977) by following the procedure shown in scheme 1 to give the neutral fractions.

Thus, the whole volatile components were placed in the fractionation funnel and 100 ml of a 5% HCl solution were added thereto followed by vigorous shaking.

The aqueous layer was separated from the ether layer and saturated with NaCl, and 50 ml of diethyl ether was added thereto. After vigorous stirring, the ether layer was removed and combined with the above ether layer. This procedure was repeated by using 100 ml of a 5% NaCl solution to give an ether layer, which was dried over anhydrous MgSO₄ to give the neutral fractions.

Scheme 1:
Fractionation of the volatile components

-continued
Scheme 1:
Fractionation of the volatile components (3) Gas Chromatography and Organoleptic Test of the Neutral Fractions The neutral fractions obtained in the above(2) were concentrated to about 2 ml with a rotary evaporator and then further concentrated to about 150 µl while passing nitrogen gas.

The concentrate was subjected to preparative gas chromatography, and each peak components on the gas chromatogram was organoleptically tested for its fragrance in accordance with A. Yasuhara and K. Fuwa, Bulletin of the chemical society of Japan, 50(11), 3029–3032(1977).

The conditions of gas chromatography were as follows:
  Instrument; Shimadzu GC-8A gas chromatograph
  Column; Chemically bonded fused sillica capillary column(CBP20-W12-100)
  Injector and detector temp.; 240° C.
  Column temp.; 60°–200° C. (10° C./min.)
  Carrier gas; $N_2$ (8 ml/min.)
  Range; $10^3$
  Attenuation; 1
  Detector; FID The GC-organoleptic characteristics of the neutral fractions of volatile components produced by *Bacillus subtilis* PM3 and SS9, respectively, which were cultured in a pure soybean medium were shown in FIGS. 1 and 2.

(4) Identification of the Neutral Fraction

In order to identify the aroma components of the neutral fractions of the volatile components produced by *B. subtilis* PM3 and *B. subtilis* SS9, the peaks on the gas chromatogram were subjected to GC-mass spectroscopy under the following conditions:
  Instrument; Finnigan MAT 4510B GC-mass spectrometer
  Column; Carbowax-20M-25M
  Split ratio; 30:1
  Injector temp.; 230° C.
  Detector temp.; 250° C.
  Temp. prog.; 45° C. for 2 min., 45°–220° C.(15° C./min.), and then 220° C. for 11.4 min.
  Carrier gas; He (5 ml/min.)
  Electron voltage; 70 eV
  Electron multiplier; 1100 V
  Ionizer temp.; 150° C.

The mass spectrum obtained was library searched by aid of computer and the peak components were identified by comparing the retention time thereof with the retention index listed in The Sadtier standard gas chromatography retention index library by KOVATS(1986).

Figure 3:
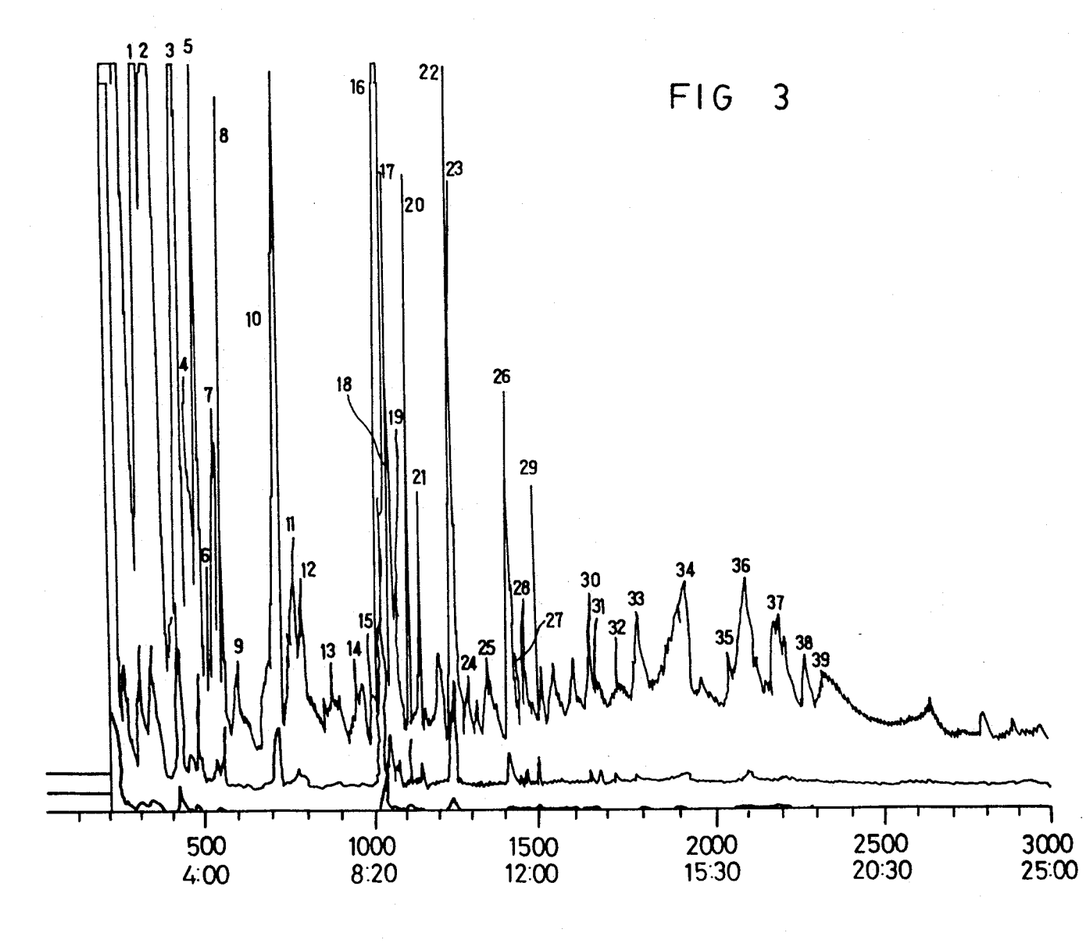
FIG. 3 is a gas chromatogram of the neutral fractions of the volatile components from *Bacillus subtilis* PM3 cultured in the pure soybean medium.
Figure 4:
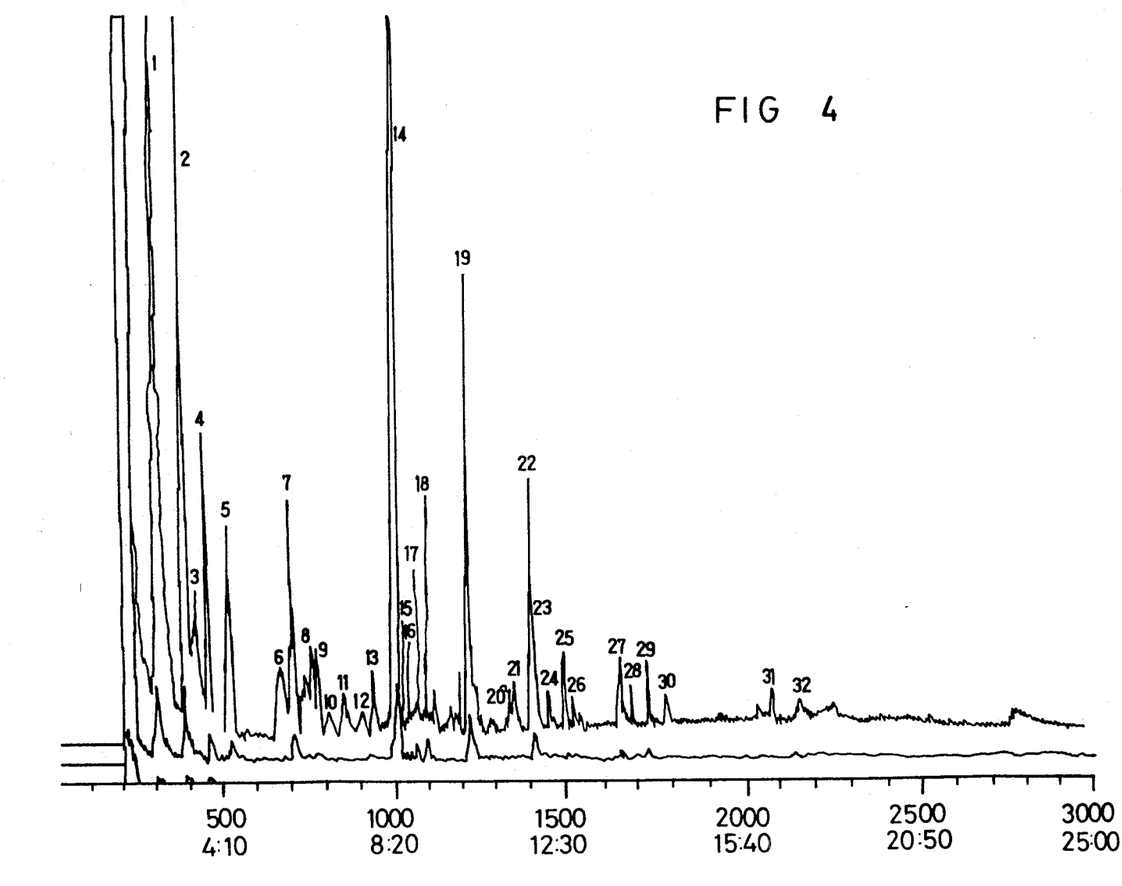
FIG. 4 is a gas chromatogram of the neutral fractions of the volatile components from *Bacillus subtilis* SS9 cultured in the pure soybean medium.

The gas chromatograms of the neutral fractions of the volatile components produced by *Bacillus subtilis* PM3 and SS9 were shown in FIGS. 3 and 4, respectively, and the compounds identified from the neutral fractions, which correspond to the peak Nos. in FIGS. 3 and 4 were listed in Table 4 and 5.

TABLE 4

The compounds identified from the neutral fraction of the volatile components produced by *B. subtilis* PM3

| Peak No. | Compound |
|---|---|
| 1 | Acetic acid, ethyl ester |
| 2 | pentanal |
| 3 | Unknown |
| 4 | 2-Methyl-2-pentanone |
| 5 | 1,3,5-Cycloheptatriene |
| 6 | Dimethyl disulfide |
| 7 | Hexanal |
| 8 | 2-Methyl-1-propanol |
| 9 | Xylene |
| 10 | 3-Methyl-1-butanol |
| 11 | (Z)-3-Penten-1-ol |
| 12 | Unknown |
| 13 | Unknown |
| 14 | Dimethyl trisulfide |
| 15 | Acetic acid |
| 16 | 7-Octen-4-ol |
| 17 | 2-Nonanone |
| 18 | Nitric acid, nonyl ester |
| 19 | Unknown |
| 20 | Benzaldehyde |
| 21 | 1-Octanol |
| 22 | 2-Furanmethanol |
| 23 | Benzeneacetaldehyde |
| 24 | Unknown |
| 25 | Naphthalene |
| 26 | (E,E)-2,4-Decadienal |
| 27 | Unknown |
| 28 | Unknown |
| 29 | Benzeneethanol |
| 30 | 1,5-bis(1,1-dimethylethyl)-3,3-dimethyl-bicyclo[3,1,0]hexan-2-one |
| 31 | Unknown |
| 32 | Nonanedioic acid |
| 33 | [R-(Z)]-12-(Acetyloxy)-9-octadecenoic acid, methyl ester |
| 34 | Hexadecanoic acid |
| 35 | Nonadecanol |
| 36 | 1-Eicosanol |
| 37 | Unknown |
| 38 | Octadecanoic acid, phenylmethyl ester |
| 39 | Unknown |

TABLE 5

The compounds identified from the neutral fraction of the volatile components produced by *B. subtilis* SS9

| Peak No. | Compound |
|---|---|
| 1 | Pentanal |
| 2 | Unknown |
| 3 | 3,7-Dimethyl-nonane |
| 4 | 1,3,5-Cycloheptatriene |
| 5 | Hexanal |
| 6 | 5-Methyl-2-hexanone |
| 7 | 3-Methyl-1-butanol |
| 8 | 3-Methyl-3-buten-1-ol |
| 9 | 5-Methyl-2-heptanone |
| 10 | 2,2,3-Trimethyl-3-oxetanol |
| 11 | 3-Methyl-2-hexanol |
| 12 | Unknown |
| 13 | Dimethyl trisulfide |
| 14 | 7-Octen-4-ol |
| 15 | 2-Decanone |
| 16 | 2-Ethyl-1-hexanol |
| 17 | 1H-Pyrrole |
| 18 | Benzaldehyde |
| 19 | Unknown |
| 20 | 2-Ethyl-2-hexen-1-ol |
| 21 | Unknown |
| 22 | (E,E)-2,2-Decadienal |
| 23 | (E)-1-(2,2,6,6-Tetramethyl-1,3-cyclohexadiene)-2-buten-1-one |
| 24 | 3-Methyl-furan |
| 25 | 2,6-Bis(1,1-imethylethyl)-4-methyl- |

TABLE 5-continued

The compounds identified from the neutral fraction of the volatile components produced by *B. subtilis* SS9

| Peak No. | Compound |
|---|---|
| | phenol |
| 26 | 1-Cyclopropyl-3-nitro-benzene |
| 27 | Unknown |
| 28 | Unknown |
| 29 | 3,5-dimethyl-1,2,4-trithiolane |
| 30 | Cyclopentaneundecanoic acid, methyl ester |
| 31 | Unknown |
| 32 | Unknown |

Figure 1:
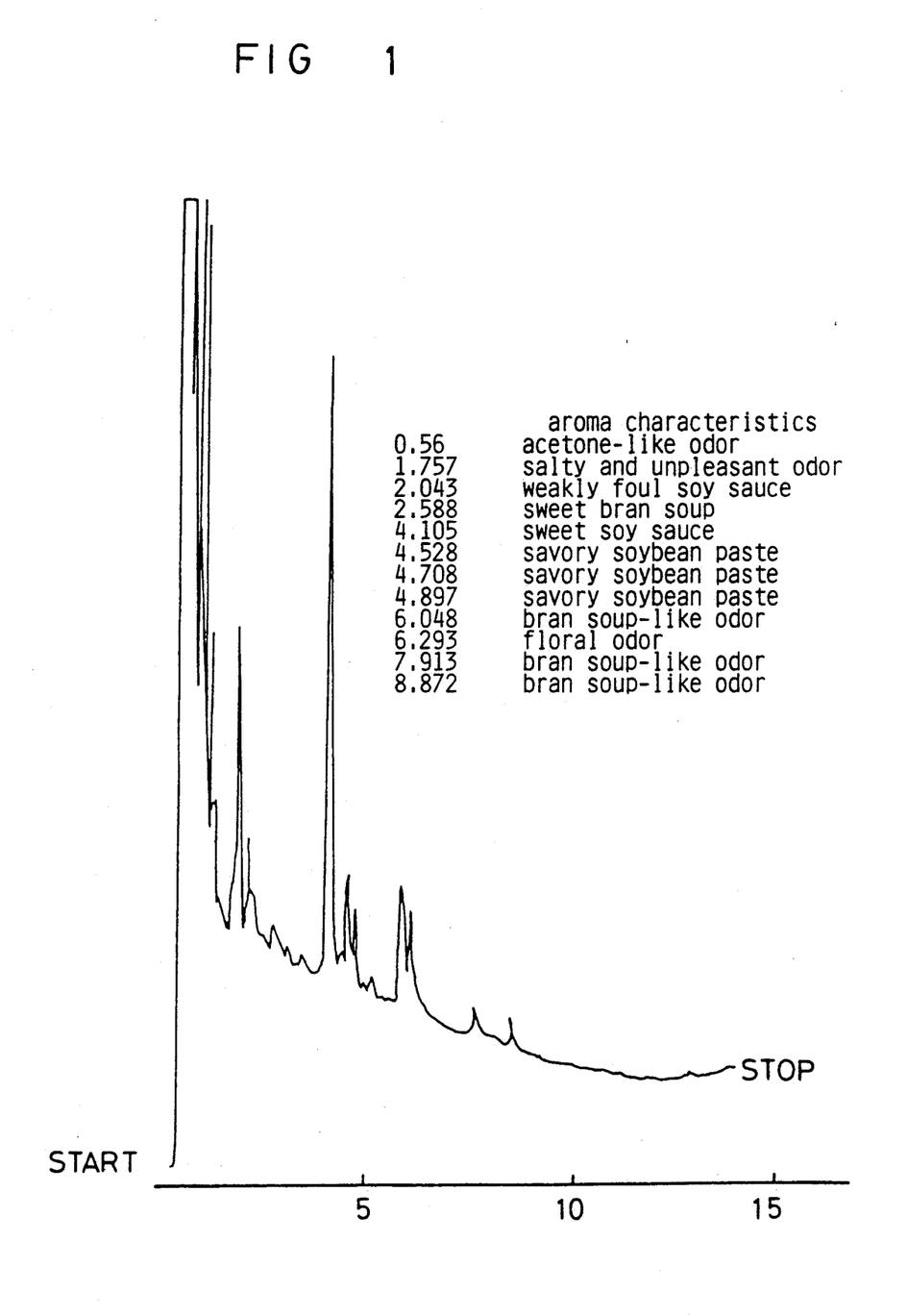
FIG. 1 is a gas chromatogram and organoleptic characteristics of the neutral fractions of volatile components from *Bacillus subtilis* PM3 cultured in the pure soybean medium.

With regard to the aroma components produced by *Bacillus subtilis* PM3, the peaks at retention times of 2.048 and 4.105 in FIG. 1, which smell of soy sauce, were identified as (Z)-3-penten-1-ol and 7-octen-4-ol corresponding to the peaks Nos. 11 and 16 in FIG. 3, respectively.

The peaks at retention times of 4.528 to 4.897 in FIG. 1, which smell of soybean paste, were identified as 2-nonanone(peak No. 17 in FIG. 3), nictric acid, nonyl ester(peak No. 18 FIG. 3), unknown(peak No. 19 in FIG. 3), benzaldehyde(peak No. 20 in FIG. 3) and 1-octanol(peak No. 21 in FIG. 3), respectively.

Figure 2:
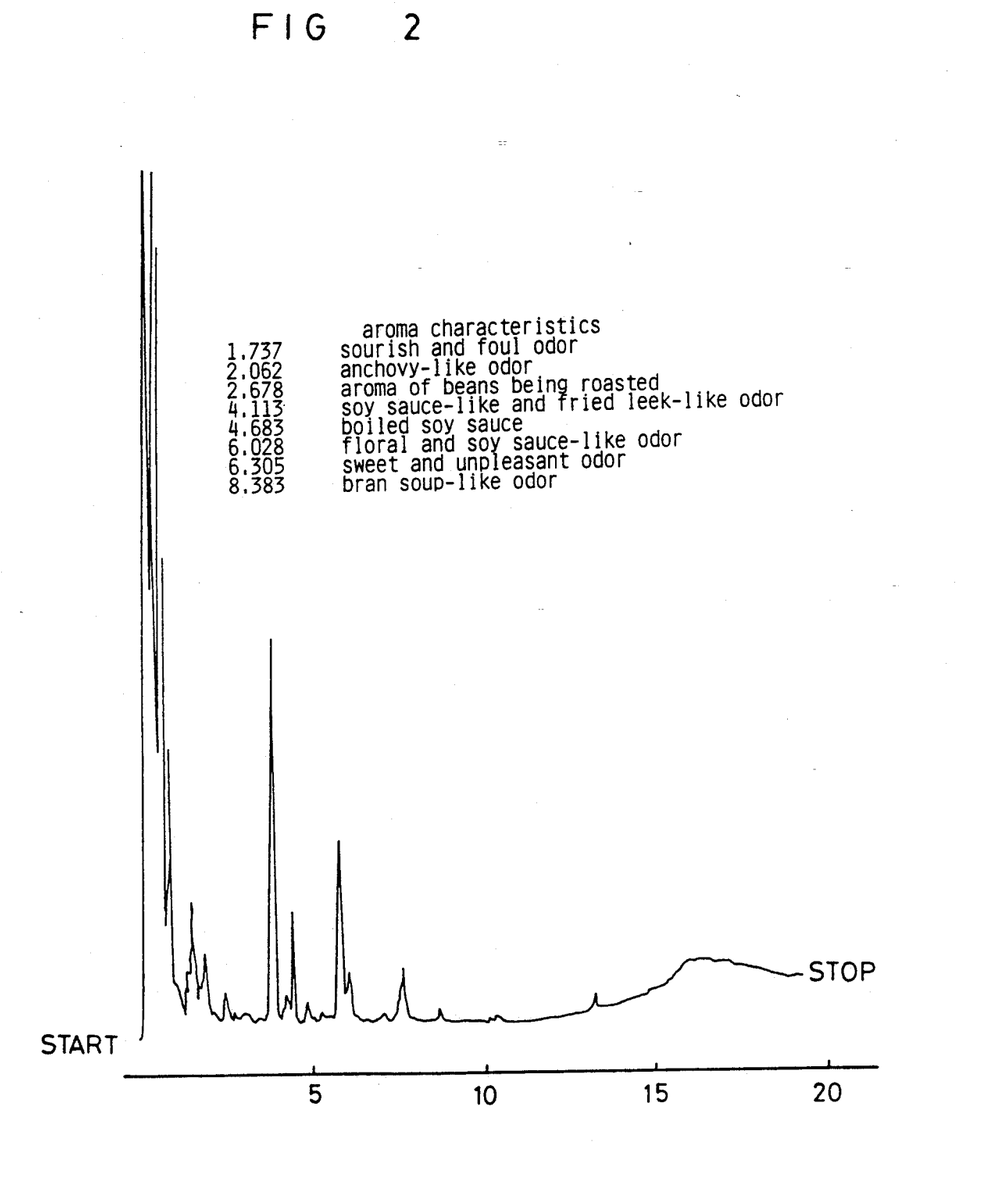
FIG. 2 is a gas chromatogram and organoleptic characteristics of the neutral fractions of volatile components from *Bacillus subtilis* SS9 cultured in the pure soybean medium.

With regard to the aroma components produced by *Bacillus subtilis* SS9, the peaks at retention times of 4. 113, 4.683 and 6.208 in FIG. 2, which smell of soy sauce, were identified as 7-octen-4-ol(peak No. 14 in FIG. 4), benzaldehyde(peak No. 18 in FIG. 4) and unknown (peak No. 19 in FIG. 4), respectively. According to the invention, *Bacillus subtilis* PM3 or *Bacillus subtilis* SS9 may be cultured in a pure boiled soybean medium together with the fusant yeast ST723-F31 or the mutant *Bacillus licheniformis* SSA3-2M1, which are available to the public from the Korean Collection for Type Culture, Daejon, Korea under the accesion number of KCTC 0012BP or KCTC 8489P, respectively, in order to prepare soybean paste.

The fusant yeast ST723-F31, a fusant of *Zygosaccharomyces rouxii* and *Torulopsis versatilis*, produces the characteristic aroma of soy sauce.

The mutant *Bacillus licheniformis* SSA3-2M1 produces the characteristic pigment of soy sauce.

The invention being generally described, a more complete understanding can be attained by reference to the examples which are provided herein for purposes of illustration only, and are not intended to limit the invention.

EXAMPLE 1

A certain amount of the home-made soy sauce and soy paste, which were aged for more than one year, were three-fold diluted with sterilized water and cultured in the isolation medium comprising a beef extract 0.1%, peptone 1.0%, glucose 1.0%, NaCl 2.0% and agar 2.0% (pH 7.0) to prepare the pure cultures of *Bacillus subtilis* PM3 and *Bacillus subtilis* SS9. Besides, a pure boiled soybean medium was prepared as follows: 200 g of soybean were immersed in water for 16 hours, boiled at 106° C. for 3 hours and smashed. The ratio of water to the smashed soybeans was adjusted to about 2.5:1. Salt was added to the concentration of 10% of water content. 300 g of the smashed boiled soybeans were placed in a 500 ml flask and sterilized with the steam under the pressure of 15 atm. at 121° C. for 40 min.

The pure cultured *B. subtilis* PM3 or SS9 was cultured in the above pure boiled soybean medium at 30° C. for 40 days to produce soybean paste. During the cultivation, the colour of the culture broth after culturing for 10, 20 and 30 days were tested by the trained panel. And the color and aroma of the soybean paste before and after boiling were also tested. The results were shown in Table 6.

TABLE 6

The quality of the soybean paste

| Strain | Color of the culture broth after culturing for | | | Aroma of the soybean paste | After boiling | | pH |
|---|---|---|---|---|---|---|---|
| | 10 days | 20 days | 30 days | | Aroma | Flavor | |
| PM3 | yellow oak | light yellow oak | light yellow oak | savory fermented soybeans odor | traditional korean soy sauce odor | soybean paste taste | 7.54 |
| SS9 | yellow oak | yellow oak | yellow oak | sweet walnut odor | soybean paste odor | soybean paste taste | 7.44 |

EXAMPLE 2

*Bacillus subtilis* PM3 or *Bacillus subtilis* SS9 was cultured in the pure boiled soybean medium prepared in Example 1 at 30° C. for 40 days or 55 days to produce soybean paste, and the colour and aroma of the soybean paste before and after boiling were tested by the trained panel. The results were shown in Table 7.

TABLE 7

The quality of the soybean paste depending on the cultivation time

| Strain | Cultivation time | Color of the soybean paste (Surface) (Bottom) | pH | Aroma of the soybean paste | After boiling | |
|---|---|---|---|---|---|---|
| | | | | | Aroma | Flavor |
| PM3 | 40 | yellow oak light khaki | 6.65 | sweet and delicate soybean paste odor | weak soybean paste odor | tasteless |
| | 55 | cinnamon yellow oak | 7.61 | savory soybean paste and weak bean oil odor | weak soybean paste odor | tasteless |
| SS9 | 40 | yellow oak light khaki | 7.45 | weakly unpleasant and savory bean oil odor | fermenting soybean paste odor | unpleasant soybean paste taste |

TABLE 7-continued

| Strain | Cultivation time | Color of the soybean paste (Surface) (Bottom) | pH | Aroma of the soybean paste | After boiling Aroma | Flavor |
|---|---|---|---|---|---|---|
| | 55 | cinnamon yellow oak | 7.54 | savory bean oil odor | boiled beans odor | soybean paste taste |

EXAMPLE 3

*Bacillus subtilis* SS9 or *Bacillus subtilis* PM3 was cultured together with the fusant yeast ST723-F31 (KCTC 0012BP) prepared from *Zygosaccharomyces rouxii* and *Torulopsis versatilis* in the pure boiled soybean medium prepared in Example 1 at 30° C. for 40 days to produce soybean paste. The color and aroma of the soybean paste before and after boiling were tested by the trained panel, and the results were shown in Table 8.

TABLE 8

The quality of the soybean paste produced by *B. subtilis* PM3 or SS9 plus fusant yeast ST723-F31 cultured in the pure boiled soybean medium

| strain | Color of the soybean paste | pH | Aroma of the soybean paste | After boiling Aroma | Flavor |
|---|---|---|---|---|---|
| PM3 + ST723-F31 | light khaki | 7.60 | sweet-scented and weakly foul soybean paste odor | weakly salty soybean paste odor | salty and weak soybean paste taste |
| SS9 + ST723-F31 | light khaki | 7.40 | sweet-scented fermented soybean odor | weak soybean paste odor | salty taste |

EXAMPLE 4

*Bacillus subtilis* SS9 or *Bacillus subtilis* PM3 was cultured in the pure boiled soybean medium prepared in Example 1 while inoculating the culture broth with the fusant yeast ST723-F31 after culturing 10, 20 or 30 days. The cultivation was carried out at 30° C. for 40 days to produce soybean paste. The color and aroma of the soybean paste before and after boiling were tested by the trained panel, and the results were shown in Table 9.

TABLE 9

The quality of the soybean paste depending on the time at which the fusant yeast ST723-F31 is inoculated

| Strain | Fusant yeast is inoculated after culturing for | Color of the soybean paste (surface) (Bottom) | pH | Aroma of the soybean paste | After boiling Aroma | Flavor |
|---|---|---|---|---|---|---|
| PM3 | 10 days | light khaki light khaki | 7.20 | refreshing and weak soybean paste odor | sweet-scented odor | salty soybean paste taste |
| | 20 days | khaki light khaki | 7.50 | refreshing and weakly sweet-scented soybean paste odor | soybean paste odor | salty soybean paste taste |
| | 30 days | light khaki light khaki | 7.50 | refreshing and weakly foul soybean paste odor | sweet soybean paste odor | weakly sweet and bitter soybean paste taste |
| SS9 | 10 days | light khaki light khaki | 7.94 | weakly sweet and sweet-scented soybean paste odor | weak soybean paste odor | soybean paste taste |
| | 20 days | light khaki light khaki | 7.21 | sweet-scented and weakly unpleasant soybean paste odor | weak soybean paste odor | salty and weak soybean paste taste |
| | 30 days | light khaki light khaki | 7.15 | sweet-scented soybean paste odor | weak soybean paste odor | salty and weak soybean paste taste |

EXAMPLE 5

*Bacillus subtilis* PM3 was cultured together with *Bacillus licheniformis* SSA3-2M1(KCTC 8489P) in the pure boiled soybean medium prepared in Example 1 at 30° C. for 40 days to produce soybean paste. The color and aroma of the soybean paste before and after boiling were tested by the trained panel, and the results were shown in Table 10.

TABLE 10

The quality of the soybean paste produced by *B. subtilis* PM3 plus *B. licheniformis* SSA3-2M1

| Color of the soybean paste | pH | Aroma of the soybean paste | After boiling Aroma | Flavor |
|---|---|---|---|---|
| Surface: yellow oak Bottom: yellow oak | 7.11 | weakly unpleasant soybean paste odor | weak soy sauce odor | weakly salty fermented soybeans |

TABLE 10-continued

The quality of the soybean paste produced by B. subtilis PM3 plus B. licheniformis SSA3-2M1

| Color of the soybean paste | pH | Aroma of the soybean paste | After boiling Aroma | Flavor |
|---|---|---|---|---|
| | | | | taste |

EXAMPLE 6

*Bacillus subtilis* PM3 and *Bacillus licheniformis* SSA3-2M1 were cultivated together in the pure boiled soybean medium prepared in Example 1 while inoculating the culture broth with the fusant yeast ST723-F31 after culturing 0, 10, 20 or 30 days. The cultivation was carried out at 30° C. for 40 days to produce soybean paste. The color and aroma of the soybean paste before and after boiling were tested by the trained panel, and the results were shown in Table 11.

TABLE 11

The quality of the soybean paste depending on the time at which the fusant yeast ST723-F31 is inoculated

| Fusant yeast is inoculated after culturing for | Color of the soybean paste | pH | Aroma of the soybean paste | After boiling Aroma | Flavor |
|---|---|---|---|---|---|
| 0 day | yellow oak | 7.50 | sweet-scented soybean paste odor | weak soybean paste odor | soybean paste taste |
| 10 days | yellow oak | 7.68 | weakly unpleasant soybean paste odor | soybean paste and weak soy sauce odor | pleasant soybean paste taste |
| 20 days | yellow oak | 7.37 | weak ammonia and soybean paste odor | weak soybean paste odor | weakly bitter soybean paste taste |
| 30 days | yellow oak | 7.61 | ammonia and sweet-scented soybean odor | weak soybean paste odor | weakly bitter soybean paste taste |

EXAMPLE 7

*Bacillus subtilis* PM3 or *Bacillus subtilis* SS9 was cultured alone or together with the fusant yeast ST723-F31 in the pure boiled defatted soybean medium at 30° C. for 40 days to produce soybean paste. The pure boiled defatted soybean medium was prepared by the same procedure as in Example 1 except that defatted soybeans were employed. The colour and aroma of the soybean paste before and after boiling were tested by the trained panel, and the results were shown in Table 12.

TABLE 12

The quality of the soybean paste produced by B. subtilis PM3 or SS9 alone or together with fusant yeast ST723-F31 cultured in the pure boiled defatted soybean medium for 40 days.

| Strain | Color of the soybean paste (Surface) (Bottom) | pH | Aroma of the soybean paste | After boiling Aroma | Flavor |
|---|---|---|---|---|---|
| PM3 | dark brown dark brown | 7.73 | unpleasant and weak soy sauce odor | weakly sweet-scented soybean paste odor | bitter and weak soybean paste taste |
| PM3 + ST723-F31 | dark brown dark brown | 7.72 | weakly savory and unpleasant soybean paste odor | weakly sweet-scented soybean odor | weak soybean paste taste |
| SS9 | dark brown gold brown | 7.93 | weakly unpleasant soybean paste odor | weakly sweet-scented soybean paste odor | bitter and weak soybean paste taste |
| SS9 + ST723-F31 | dark brown dark brown | 7.65 | MISO-like odor | weakly bitter odor | bitter and weak soybean paste taste |

EXAMPLE 8

*Bacillus subtilis* PM3 or *Bacillus subtilis* SS9 was cultured alone or together with the fusant yeast ST723-F31 in the pure boiled cotyledonous soybean medium at 30° C. for 40 days to produce soybean paste. The pure boiled cotyledonous soybean medium was prepared by the same procedure as in Example 1 except that cotyledonous soybeans were employed. The color and aroma of the soybean paste before and after boiling were tested by the trained panel, and the results were shown in Table 13.

TABLE 13

The quality of the soybean paste produced by *B. subtilis* PM3 or SS9 alone or together with fusant yeast ST723-F31 cultured in the pure boiled cotyledonous soybean medium

| Strain | Color of the soybean paste (Surface) (Bottom) | pH | Aroma of the soybean paste | After boiling Aroma | Flavor |
|---|---|---|---|---|---|
| PM3 | cinnamon yellow oak | 7.72 | savory and fermenting soybean paste odor | weak and fermenting soybean paste odor | weak soybean paste taste |
| PM3 + ST723-F31 | cinnamon yellow oak | 7.71 | sweet and sweet-scented and fermenting soybean paste odor | weak and fermenting soybean paste odor | weakly bitter soybean paste taste |
| SS9 | gold brown yellow oak | 7.93 | sweet-scented and fermenting soybean paste odor | weakly sweet-scented soybean paste odor | soybean paste taste |
| SS9 + ST723-F31 | gold brown yellow oak | 7.55 | weakly unpleasant korean soybean paste odor | weakly sweet-scented soybean paste odor | weakly salty soybean paste taste |

EXAMPLE 9

*Bacillus subtilis* PM3 or *Bacillus subtilis* SS9 was cultured alone or together with the fusant yeast ST723-F31 in the pure boiled defatted soybean medium prepared in Example 7 at 30° C. for 58 days to produce soybean paste.

The color and aroma of the soybean paste before and after boiling were tested by the trained panel, and the results were shown in Table 14.

EXAMPLE 10

*Bacillus subtilis* PM3 or *Bacillus subtilis* SS9 was cultured alone or together with the fusant yeast ST723-F31 in the pure boiled cotyledonous soybean medium prepared in Example 8 at 30° C. for 58 days to produce soybean paste.

The color and aroma of the soybean paste before and after boiling were tested by the trained panel, and the results were shown in Table 15.

TABLE 14

The quality of the soybean paste produced by *B. subtilis* PM3 or SS9 alone or together with fusant yeast ST723-F31 cultured in the pure boiled defatted soybean medium for 58 days

| Strain | Color of the soybean paste (Surface) (Bottom) | pH | Aroma of the soybean paste | After boiling Aroma | Flavor |
|---|---|---|---|---|---|
| PM3 | dark brown dark brown | 7.87 | MISO-like sweet and weak soy sauce odor | soybean paste odor | salty soybean paste taste |
| PM3 + ST723-F31 | sepia sepia | 7.71 | unpleasant soybean paste odor | soybean paste odor | weakly bitter soybean paste taste |
| SS9 | dark brown dark brown | 7.90 | weakly unpleasant soybean paste odor | weak salty soybean paste odor | bitter soybean paste taste |
| SS9 + ST723-F31 | sepia sepia | 7.78 | weakly unpleasant soybean paste odor | sweet diluted soybean paste odor | bitter and weak soybean paste taste |

TABLE 15

The quality of the soybean paste produced by *B. subtilis* PM3 or SS9 alone or together with fusant yeast ST723-F31 cultured in the pure cotyledonous soybean medium for 58 days

| Strain | Color of the soybean paste (Surface) (Bottom) | pH | Aroma of the soybean paste | After boiling Aroma | Flavor |
|---|---|---|---|---|---|
| PM3 | gold brown yellow oak | 7.69 | MISO-like sweet odor | weak soybean paste odor | soybean paste taste |
| PM3 + ST723-F31 | gold brown yellow oak | 7.74 | weakly sweet soybean paste odor | soybean paste odor | salted soybean paste taste |
| SS9 | gold brown yellow oak | 7.44 | weakly unpleasant fermenting soybean paste odor | soybean paste odor | soybean paste taste |
| SS9 + ST723-F31 | gold brown yellow oak | 7.67 | weakly salty traditional soybean paste odor | soybean paste odor | soybean paste taste |

As can be seen from the above, the process for the production of Korean traditional soybean paste according to the invention, which comprises inoculating a pure boiled soybean medium with *Bacillus subtilis* PM3 or *Bacillus subtilis* SS9 alone or together with the fusant yeast ST723-F31 or *Bacillus licheniformis* SSA3-2M1 and culturing the strain(s) at 25° to 35° C. for 40 to 60 days to produce the soybean paste, have advantages that, first, since the cultivation takes about 40 to 60 days, the soybean paste may be prepared in a remarkably shortened time compared with the conventional method which takes at least 6 to 7 months; second, the soybean paste may be prepared by a simple process; third, the standardization of the quality of the soybean paste is possible by a controlled use of the certain strains; i.e., inoculating a boiled soybean medium with newly isolated strain of *Bacillus subtilis* PM3 or *Bacillus subtilis* SS9 alone, or together with *Bacillus licheniformis*, SSA3-2M1 or the fusant yeast ST723-F31 and culturing at 25°–35° C. for 40–60 days, and fourth, the soybean paste may be prepared on an industrial scale.

What is claimed is:

1. A method for preparing soybean paste, which comprises inoculating a boiled soybean medium with a strain of *Bacillus subtilis* PM3 (KCTC 0025BP) or *Bacillus subtilis* SS9 (KCTC 0026BP) and culturing the strain at 25° to 35° C. for 40 to 60 days to produce the soybean paste.

2. The method for preparing soybean paste according to claim 1, wherein the boiled soybean medium is a pure smashed boiled soybean medium, pure smashed boiled defatted soybean medium or pure smashed boiled cotyledonous soybean medium.

3. A method for preparing soybean paste, which comprises inoculating a boiled soybean medium with a strain of *Bacillus subtilis* PM3 (KCTC 0025BP) or *Bacillus subtilis* SS9 (KCTC 0026BP) together with a fusant yeast ST723-F31 (KCTC 0012BP) or *Bacillus licheniformis* SSA3-2M1 (KCTC 8489P) and culturing them at 25° to 35° C. for 40 to 60 days to produce the soybean paste.

4. A method according to claim 3, wherein the soybean medium is inoculated with a mixture of the strain of *Bacillus subtilis* and the yeast fusant.

5. A method according to claim 3, wherein the soybean medium is inoculated with a mixture of the strain of *Bacillus subtilis* and the *Bacillus licheniformis* SSA3-2M1.

6. A method according to claim 1, wherein the soybean medium is inoculated with a strain of *Bacillus subtilis* PM3 (KCTC 0025BP).

7. A method according to claim 1, wherein the soybean medium is inoculated with a strain of *Bacillus subtilis* SS9 (KCTC 0026BP).

* * * * *